United States Patent
Brown

(10) Patent No.: US 7,360,730 B2
(45) Date of Patent: Apr. 22, 2008

(54) MEDICAL WASTE DISPOSAL DEVICE

(75) Inventor: James S. Brown, Winfield, MO (US)

(73) Assignee: B&P Technologies, Inc., Winfield, MO (US)

( * ) Notice: Subject to any disclaimer, the term of this patent is extended or adjusted under 35 U.S.C. 154(b) by 292 days.

(21) Appl. No.: 10/891,396

(22) Filed: Jul. 14, 2004

(65) Prior Publication Data
US 2006/0014996 A1    Jan. 19, 2006

(51) Int. Cl.
B02C 17/02    (2006.01)
(52) U.S. Cl. .......................... 241/92; 241/606
(58) Field of Classification Search ................ 241/606, 241/242, 91, 100, 92
See application file for complete search history.

(56) References Cited

U.S. PATENT DOCUMENTS

| | | |
|---|---|---|
| 3,958,765 A | 5/1976 | Musselman |
| 4,905,916 A | 3/1990 | Sorwick et al. |
| 4,971,261 A | 11/1990 | Solomons |
| 4,979,683 A | 12/1990 | Busdeker |
| 5,046,669 A | 9/1991 | Wallace et al. |
| 5,054,696 A | 10/1991 | Mennel et al. |
| 5,148,004 A | 9/1992 | Gettig et al. |
| 5,168,612 A | 12/1992 | Schultz et al. |
| 5,186,397 A | 2/1993 | Orlando |
| 5,186,402 A | 2/1993 | Lin |
| 5,205,497 A | 4/1993 | Deklerow |
| 5,236,135 A | 8/1993 | Wilson et al. |
| 5,240,187 A | 8/1993 | Wilson |
| 5,340,036 A | 8/1994 | Riley |
| 5,340,039 A | 8/1994 | Lefevre |
| 5,346,142 A | 9/1994 | Miller et al. |
| 5,362,443 A | 11/1994 | Tanaka et al. |
| 5,397,068 A | 3/1995 | Solomons et al. |
| D357,261 S | 4/1995 | Morgan |
| 5,429,315 A | 7/1995 | Wollert et al. |
| 5,441,622 A | 8/1995 | Langford |
| 5,495,988 A | 3/1996 | Follese et al. |
| 5,516,052 A | 5/1996 | Adams et al. |
| 5,520,888 A | 5/1996 | Berndt |
| 5,533,681 A | 7/1996 | Riley |
| 5,543,111 A | 8/1996 | Bridges et al. |
| 5,580,521 A | 12/1996 | Gagne |
| 5,620,654 A | 4/1997 | Mosenson |
| 5,623,762 A | 4/1997 | White |
| 5,641,423 A | 6/1997 | Bridges et al. |
| 5,660,338 A | 8/1997 | Emmerson |
| 5,761,975 A | 6/1998 | Waluda |
| 5,769,336 A | 6/1998 | Emmerson |
| 5,833,922 A | 11/1998 | Held et al. |
| 5,887,807 A | 3/1999 | Beinecke |
| 5,915,636 A | 6/1999 | Caballero |
| 5,979,275 A | 11/1999 | Waluda |
| 6,027,055 A * | 2/2000 | Doskocil ..................... 241/55 |

(Continued)

*Primary Examiner*—Faye Francis
(74) *Attorney, Agent, or Firm*—Polsinelli Shalton Flanigan Suelthaus PC

(57) ABSTRACT

A medical waste disposal device having a blade that rotates and chops medical waste into chips and other small particles. The blade includes at least one opening with at least one sharpened edge. The blade also has at least one raised portion adjacent to the sharpened edges. The blade cooperates with a cutting plate to chop or scissor the medical waste. The raised portion pushes chopped medical waste away from the blade and the cutting plate.

26 Claims, 16 Drawing Sheets

U.S. PATENT DOCUMENTS

| | | |
|---|---|---|
| 6,158,314 A | 12/2000 | Thead et al. |
| 6,394,373 B1 * | 5/2002 | Morris ........................ 241/92 |
| 6,435,432 B1 * | 8/2002 | Doskocil ..................... 241/92 |
| 6,641,066 B2 | 11/2003 | Kamiya |
| 6,910,648 B1 * | 6/2005 | Reinhold ..................... 241/92 |
| 2004/0108398 A1 * | 6/2004 | Lepage ........................ 241/55 |
| 2005/0236502 A1 * | 10/2005 | Anderson et al. ...... 241/46.013 |

* cited by examiner

MEDICAL WASTE DISPOSAL DEVICE

FIELD OF THE INVENTION

The present invention relates to a medical waste disposal device having a blade that rotates and chops medical waste, such as syringes, into chips and other small particles.

BACKGROUND OF THE INVENTION

Medical waste disposal is a concern for both the medical industry and the sanitation industry. The medical industry creates an enormous amount of medical waste. Moreover, medical waste, such as syringes, catheters, tracheotomy tubes, blades, and surgical needles, may be contaminated with bacteria and/or viruses, and accordingly, proper disposal of the medical waste requires extra measures and steps beyond general waste disposal procedures. Medical waste contaminated with bacteria and/or viruses must be handled carefully by medical providers and sanitation workers to prevent their exposure to the bacteria and/or viruses.

Besides concerns regarding contamination, medical waste should be reduced in size to conserve landfill space, to reduce the labor involved in disposing the medical waste, and to reduce the amount of space that medical facilities must dedicate to waste management.

Medical waste, when properly sterilized and separated, may also be recycled. Plastics and metal form most of the constituent parts of syringes, catheters, tracheotomy tubes, blades and surgical needles.

There have been many attempts in the prior art to provide for a medical waste disposal device that grinds or reduces medical waste. Unfortunately, many of the prior art designs are inoperable or are prone to jamming. Moreover, many of these prior art devices are too large or too expensive to be suitable for an individual hospital room. Other shortcomings in the prior art include a failure to provide for a working and portable medical waste disposal device.

As described above, there is a need for a medical waste disposal device that provides for sanitary and efficient operation and further provides the potential for recycling.

SUMMARY OF THE INVENTION

Embodiments, including the technical features of the invention for which protection is sought, are illustrated and described herein and include a medical waste disposal device having a blade that rotates and chops medical waste into chips and other small particles. The blade comprises at least one opening with at least one sharpened edge. The blade also has at least one raised portion adjacent to the sharpened edges. The blade cooperates with a cutting plate to chop or scissor the medical waste. The raised portion pushes chopped medical waste away from the blade and the cutting plate. The chopped medical waste is generally forced through the opening in the blade.

It is a further aspect of the present invention to provide a portable medical waste disposal device that operates on direct current.

It is a further aspect of the present invention to provide a medical waste disposal device that reduces contamination.

It is still a further aspect of the present invention to provide a medical waste disposal device that significantly reduces the volume of the medical waste and thereby reduces labor costs related to emptying the medical waste disposal device.

These and other aspects of the present invention are achieved herein.

BRIEF DESCRIPTION OF THE DRAWINGS

The present invention is illustrated by the embodiments shown in the drawings, in which.

DETAILED DESCRIPTION OF THE INVENTION

Figure 1:
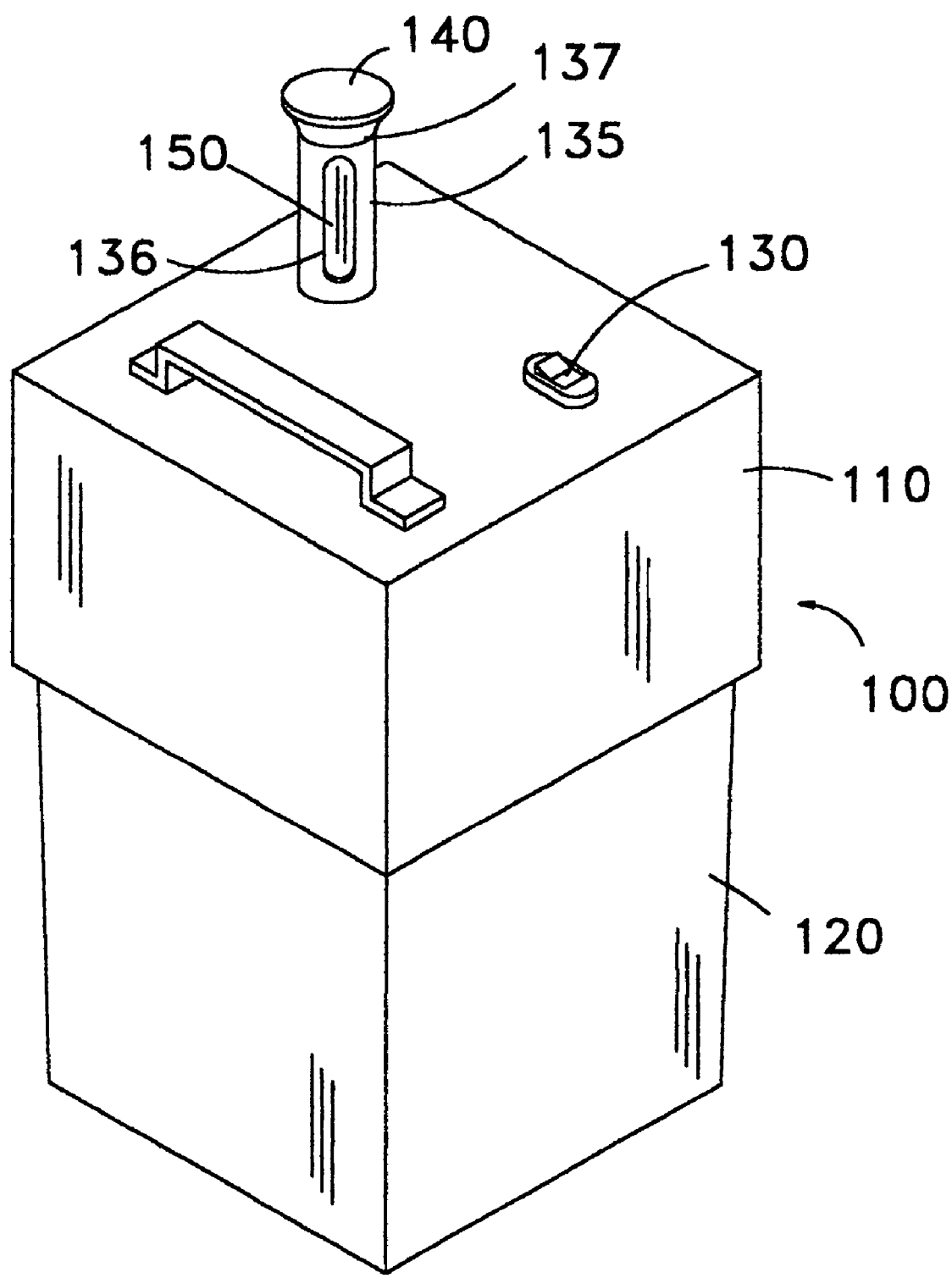
FIG. 1 is a view of a medical waste disposal device.

Referring now to the following description and figures, there are shown preferred embodiments for the medical waste disposal device of this invention, including the technical features of the invention for which protection is sought. The present invention relates to a medical waste disposal device having a blade that rotates and chops medical waste into chips and small particles. The medical waste disposal device reduces the volume of raw medical waste. Also, the medical waste disposal device may include a UV light to render the chips and small particles sterile and innocuous.

The medical waste disposal device of the present invention generally includes a housing. The housing contains the blade and means for rotating the blade safely away from the user. The housing contains the chopped medical waste until it is later disposed. In one preferred embodiment, the housing includes an upper housing and a lower housing. The upper housing includes a motor for rotating the blade. The upper housing also includes a battery for providing electrical power to the motor. Other necessary and customary electrical components and connections are also contained in or supported by the upper housing. Other embodiments may include a liner in the housing that collects the medical waste. The liner may be removed for disposal and replaced with a new liner.

On the exterior of the upper housing, an on/off switch is located for operating the device. The upper housing also includes an opening for a drop shaft and a plunger. The drop shaft provides passage for the medical waste from the exterior of the device to the blade. The plunger contains the medical waste within the drop shaft and within the housing.

The lower housing includes the blade and a space or region to collect the chopped medical waste particles. In some embodiments, an optional UV light may be contained in the lower housing or on a lower portion of the upper housing to disinfect/sterilize the chopped medical waste. In a preferred embodiment, a drive shaft from the motor penetrates the lower housing. The blade is attached to this drive shaft. The drop shaft also connects to the lower housing and has an opening into the lower housing. At the junction of the drop shaft and the lower housing, a cutting plate is provided to act in conjunction and cooperation with the blade in chopping the medical waste. The cutting plate circumscribes at least a portion of the opening of the drop shaft into the lower housing. The cutting plate includes a sharpened edge that operates in conjunction and cooperation with the blade to chop or scissor the medical waste. The sharpened edge of the cutting plate has an angle of approximately 10° to approximately 90°. This angle is shown as angle $\beta$ in FIG. 19. The cutting plate may be integral to the lower housing or may be a separate component attached to the lower housing.

In operation of the medical waste disposal device of the present invention, the operator lifts the plunger and drops the medical waste into an opening in the drop shaft where the medical waste falls in a vertical manner, due to the circumference of the drop shaft, until it contacts the blade where it is chopped by the blade and the cutting plate. An important feature of the present invention is the vertical nature of the drop shaft. This is especially important for medical waste, such as syringes, that are long and narrow. The drop shaft directs a syringe to contact the blade in a vertical manner such that the syringe is chopped in piece-by-piece manner, instead of the entire syringe contacting the blade at an instance. The drop shaft directs the syringe or the medical waste to contact the blade in a manner parallel to the axis of rotation of the blade, and thus, rotating cutting surfaces of the blade are contacting the medical waste in a perpendicular fashion. This feature reduces the likelihood of the device jamming or malfunctioning.

The blade of the present invention and its cutting surfaces will now be described. The blade, which is rotated by the motor, comprises at least one opening. Each opening is generally rectangular or ovular in shape, i.e., the opening has sides that are longer than other sides of the opening. The longer sides of the opening are generally perpendicular to the axis of rotation of the blade. Importantly, the opening also includes the sharpened edge. The blade must have at least one opening wherein the opening has a sharpened edge. The edge may be sharpened at an angle of approximately 10° to approximately 90°. This angle is shown as angle $\alpha$ in FIG. 7. In a most preferred embodiment, the edge may be sharpened to approximately 45°. The blade also includes at least one raised portion adjacent to the sharpened edge. The raised portion protrudes from the generally flat surface of the blade. The raised portion contacts the medical waste being chopped by the blade and the cutting plate and pushes it away from the cutting plate such that the chopping mechanism of the blade and the cutting plate does not jam with waste and render the device inoperable. The raised portion should be of sufficient height compared to the blade to push the chopped medical waste away from the cutting plate.

Although any number of openings may be used in the blade, preferred embodiments include approximately 2 to approximately 8 openings. In a most preferred embodiment, the blade has 4 openings. The blade may be any shape that is capable of being rotated. However, it is preferred that the blade is circular in shape. Some embodiments of the present invention include a plastic blade with metallic sharpened edges inserted therein. The blade is rotated at speeds to sufficiently chop medical waste. The blade may rotate at approximately 1000 rpm to approximately 10,000 rpm. In a preferred embodiment, the blade rotates at approximately 5,000 to approximately 6,000 rpm.

The blade is preferably made from a high carbon steel, such as, for example, a 4140 steel alloy. It is important that the blade be made of a material harder than any of the stainless steel or other metals commonly used in medical supplies such as razor blades or needles. Preferably, the high carbon steel has a rating of A-6 or higher. Preferably, the blade is made from a single piece of metal stock and/or is heat-treated.

Figure 20:
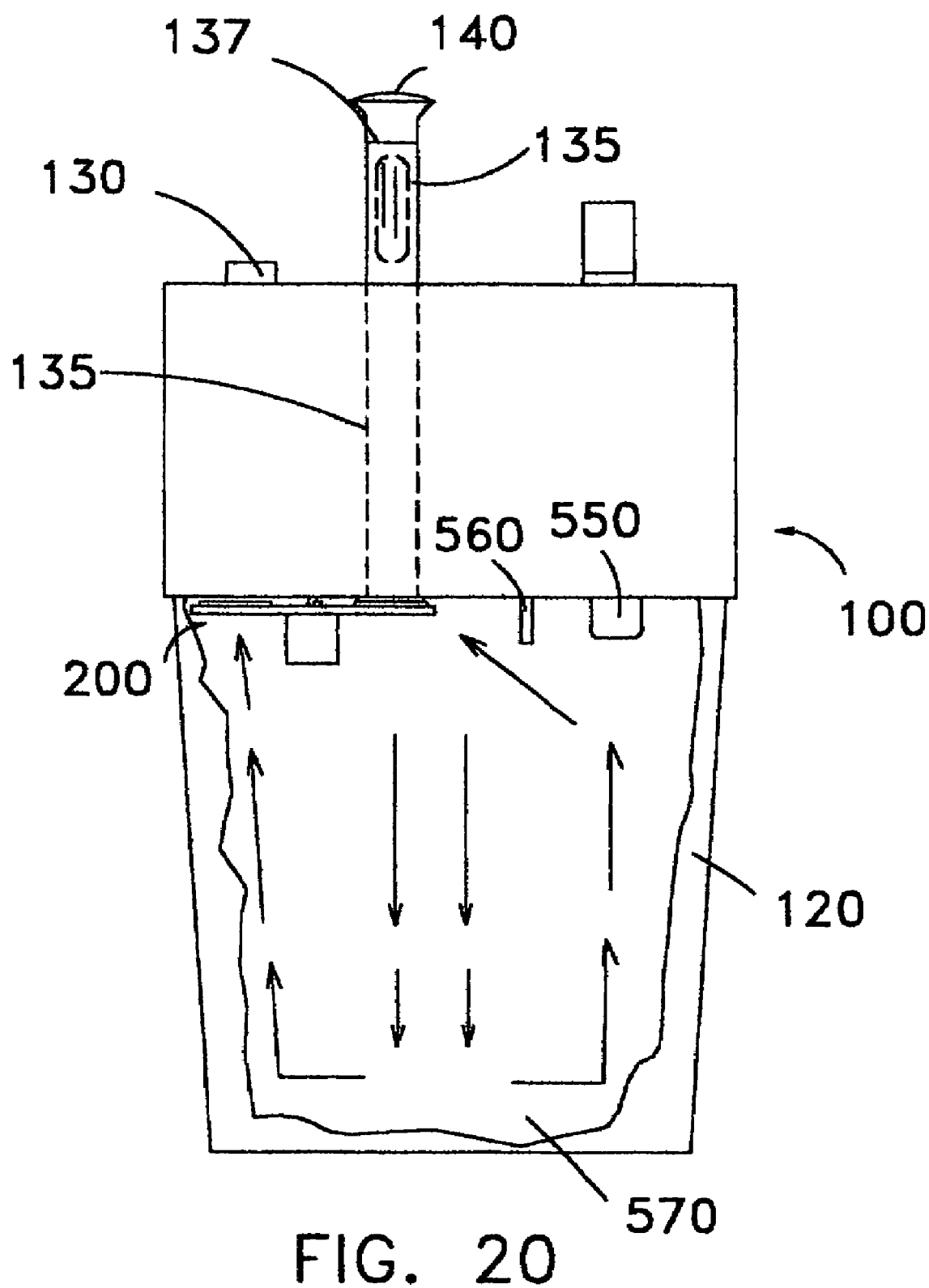
FIG. 20 is a view of the cyclonic action created by the medical waste disposal device.

As the blade is chopping the medical waste, the blade is creating a cyclonic action that creates a down draft to push the chopped particles to the bottom of the lower housing. This down draft and cyclonic action also create an up draft on peripheral edges of the lower housing and up over the blade and back again to the bottom of the lower housing. This feature is illustrated in FIG. 20. This cyclonic action is important since it also helps to reduce the jamming of the blade by keeping the blade and the cutting plate relatively free of debris and causes the medical waste to gather in the bottom of the lower housing.

Although the blade shown operates in a clockwise rotation, one of ordinary skill in the art will realize that the cutting edges of the blade and the cutting plate may be reversed, and likewise, the rotation of the blade may be reversed.

A critical feature of the present invention is the interaction of the sharpened edge of the blade, the raised portion of the blade, and the cutting plate with its sharpened edge. These three features provide for efficient chopping of the medical waste with minimal jamming of the device. The medical waste is chopped or scissored between the two sharpened edges while the raised portion pushes the chopped medical waste away from the sharpened edges and through the opening in the blade during the cutting procedure.

Another important feature of the present invention is the ability to operate on direct current. It is surprising that a device capable of chopping medical waste may be operated on direct current since, generally, such a device would need a motor too large to be operated on direct current. Most prior medical waste disposal devices are operated on alternating current. By the present invention's capability of operating on direct current, the device may be made portable and carried in ambulances or in mobile medical facilities. Direct current operation may provide for operation from a rechargeable battery source. Certain preferred embodiments operate on 12-volt direct current.

A preferred motor is commercially available from the Hansen Corporation. Specific Hansen Corporation models include the Series 21 DC motor and the Series 16 DC motor. These motors operate on 12-volt direct current. These motors are relatively small, i.e. approximately 1 and ½ inches by approximately 3 inches in size. Despite their small size, these motors generate sufficient torque, i.e., about approximately 24 ounces/inch to approximately 40 ounces/inch, which is suitable for reducing material waste.

The present invention provides for the reduction in the volume of medical waste in a ratio of about 500-to-1. This important feature reduces the amount of labor involved in the hospital setting in emptying the lower housing of its waste contents.

The upper and lower housing may be made of a hard material such as a plastic or stainless steel. A gasket may be used in the connection of the upper housing and the lower housing to provide insulation and containment of the medical waste.

The drop shaft may be a diameter of approximately one-half inch. This diameter accommodates most conventional medical waste. However, this size may vary depending on the size of the medical waste to be disposed.

A 6 watt UV germicidal bulb may prove effective for eliminating bacteria and pathogens with chopped waste. Other disinfecting bulbs and germinal products may be used.

Figure 2:
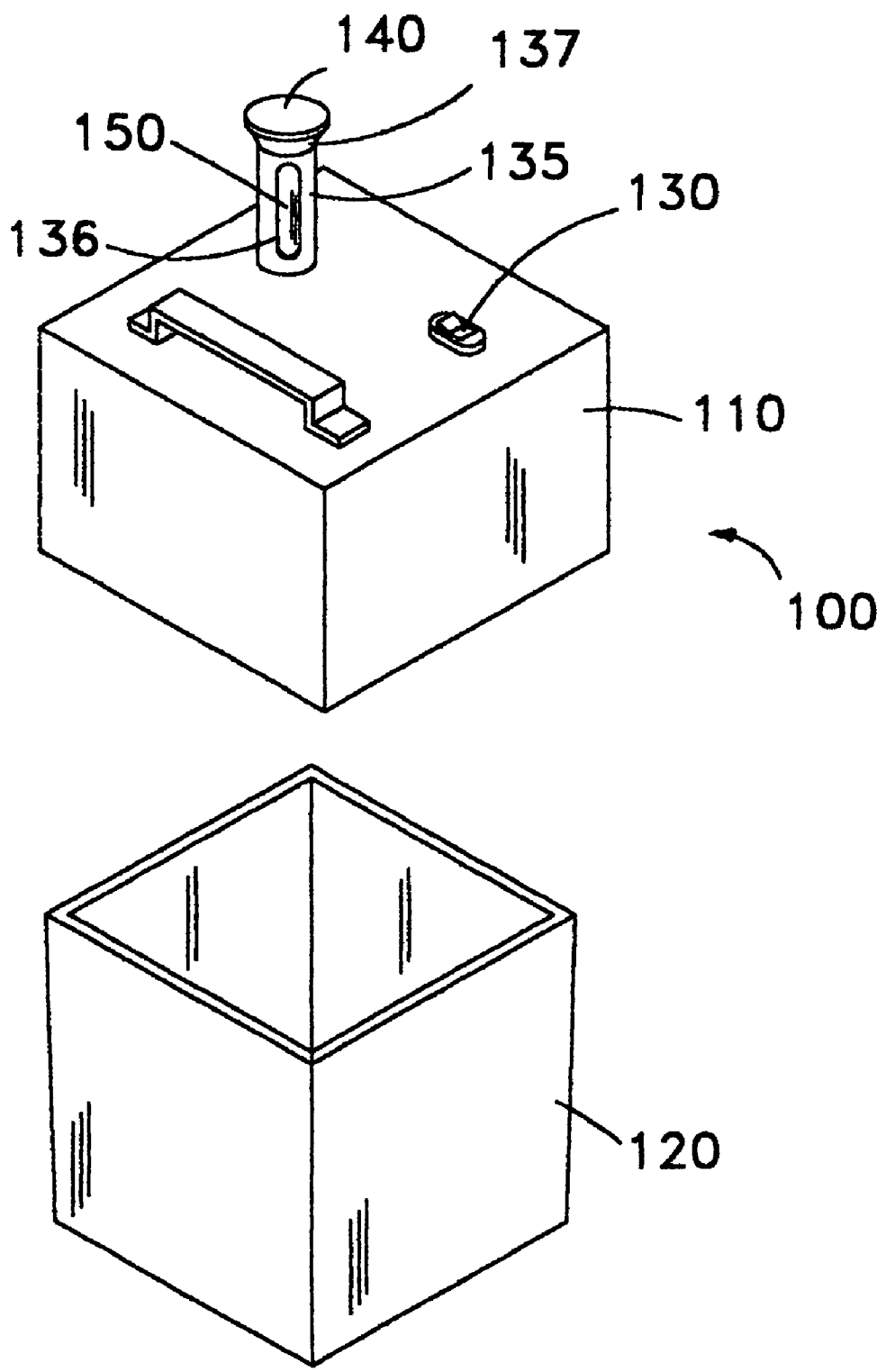
FIG. 2 is a view of the medical waste disposal device with an upper housing separated from a lower housing.
Figure 3:
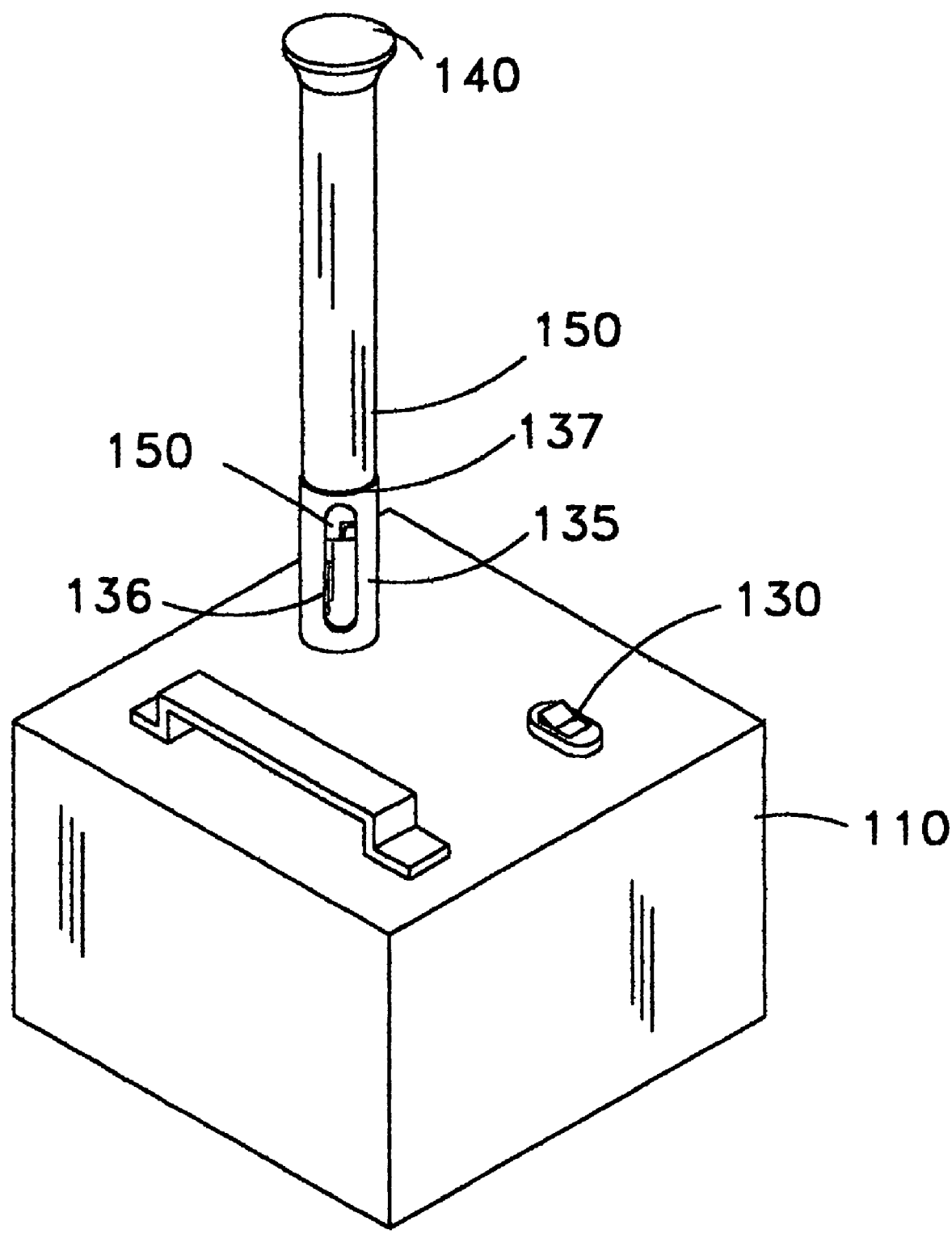
FIG. 3 is a view of the upper housing of the medical waste disposal device with a plunger removed to expose an opening in a drop shaft.

The present invention will now be described with reference to the figures:

FIGS. 1-3 are schematic representations of a medical waste disposal device 100. The medical waste disposal device 100 includes an upper housing 110 and a lower housing 120. An on/off switch 130 is shown on the upper housing 110. Protruding from the upper housing 110 is a drop shaft 135. The drop shaft 135 receives a plunger 150 through a drop shaft collar 137. A handle 140 is shown for the plunger 150. The drop shaft 135 defines a drop shaft opening 136 through which medical waste is inserted.

Figure 4:
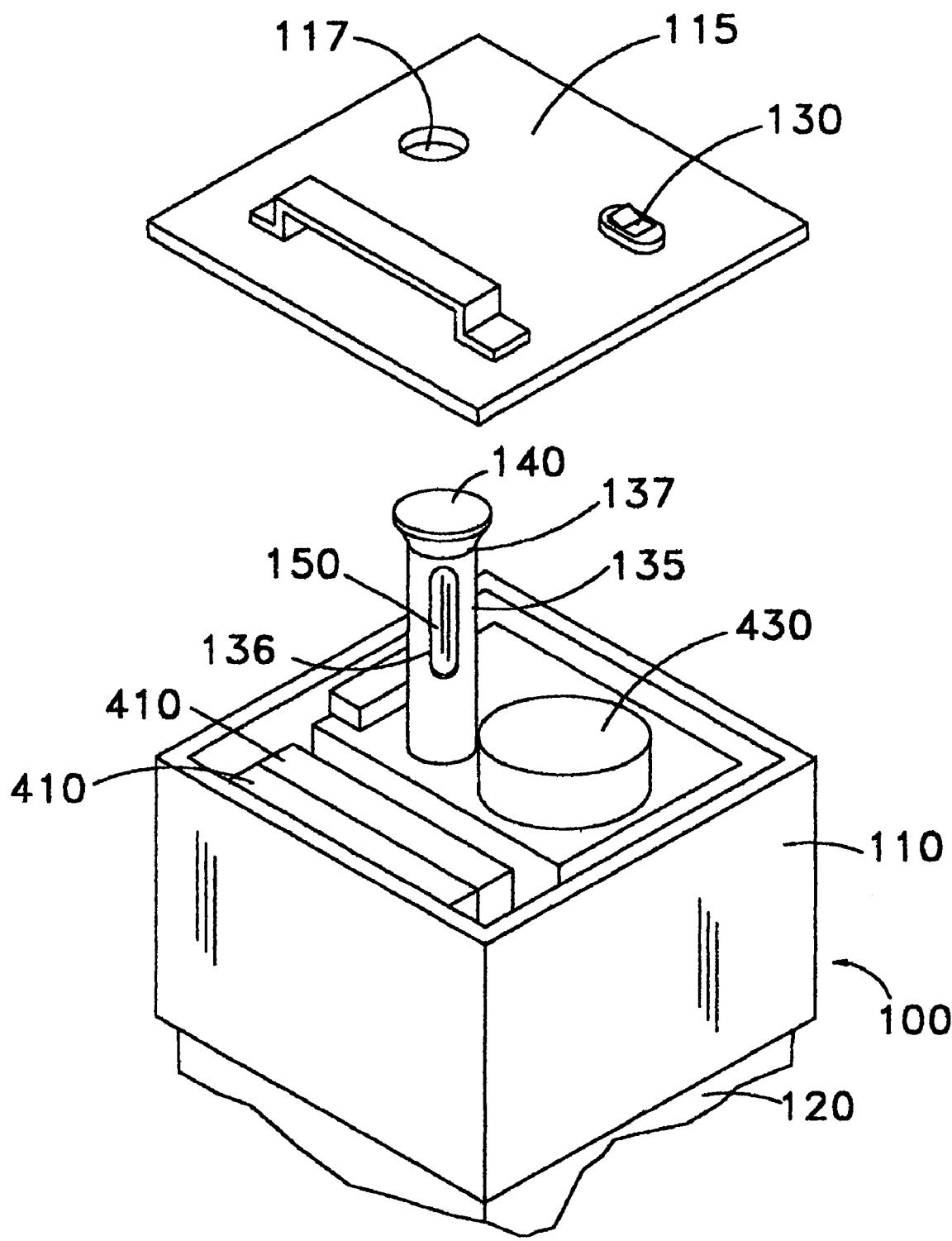
FIG. 4 is a view of the upper housing with a lid removed.

FIG. 4 is a schematic representation of an interior of the medical waste disposal device 100. A lid 115 is shown removed from the upper housing 110. The drop shaft 135 passes through a lid opening 117. A battery 410 and a motor 430 are shown in electrical connection in the interior of the upper housing 110. The upper housing 110 is penetrated by the drop shaft 135, which contains the plunger 150.

Figure 11:
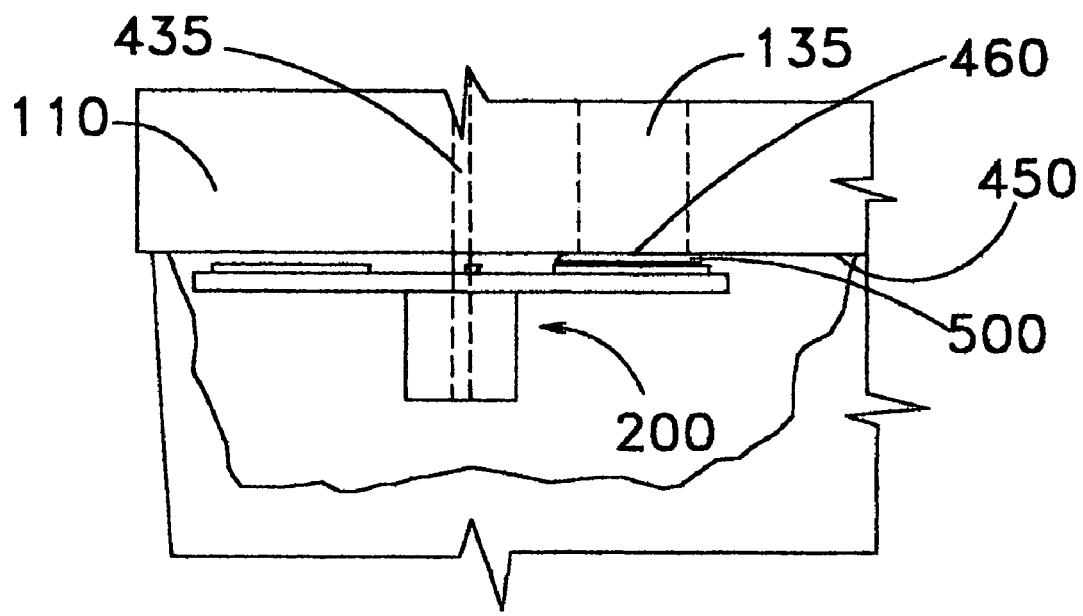
FIG. 11 is a view of the relationship of the blade to the drop shaft.
Figure 12:
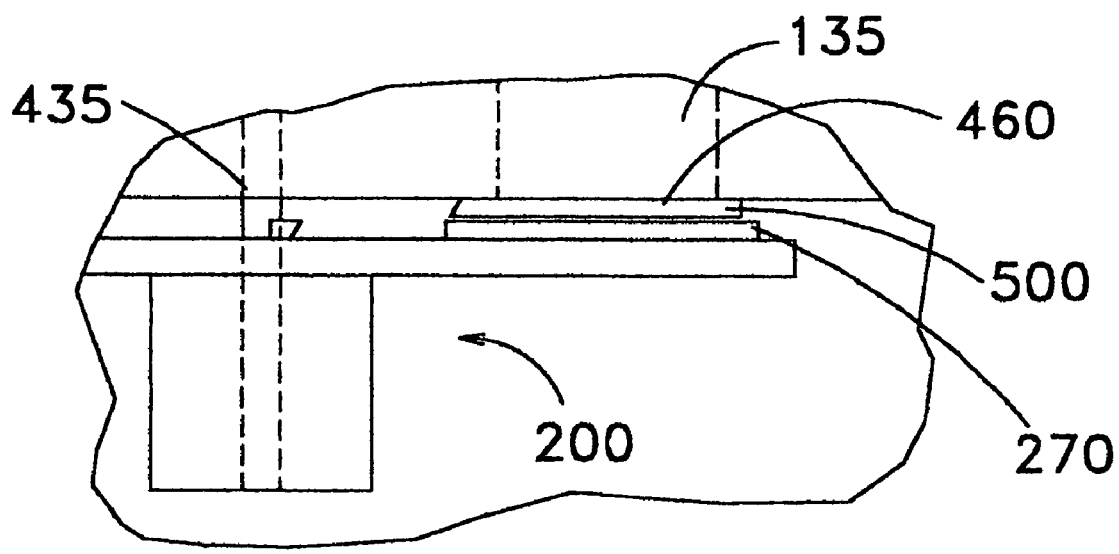
FIG. 12 is a close-up view of the relationship between the drop shaft and the blade.

The motor 430 includes a drive shaft 435 that protrudes into the lower housing 120 (shown in FIG. 11). The blade 200 is mounted or connected to the drive shaft 435.

Figure 5:
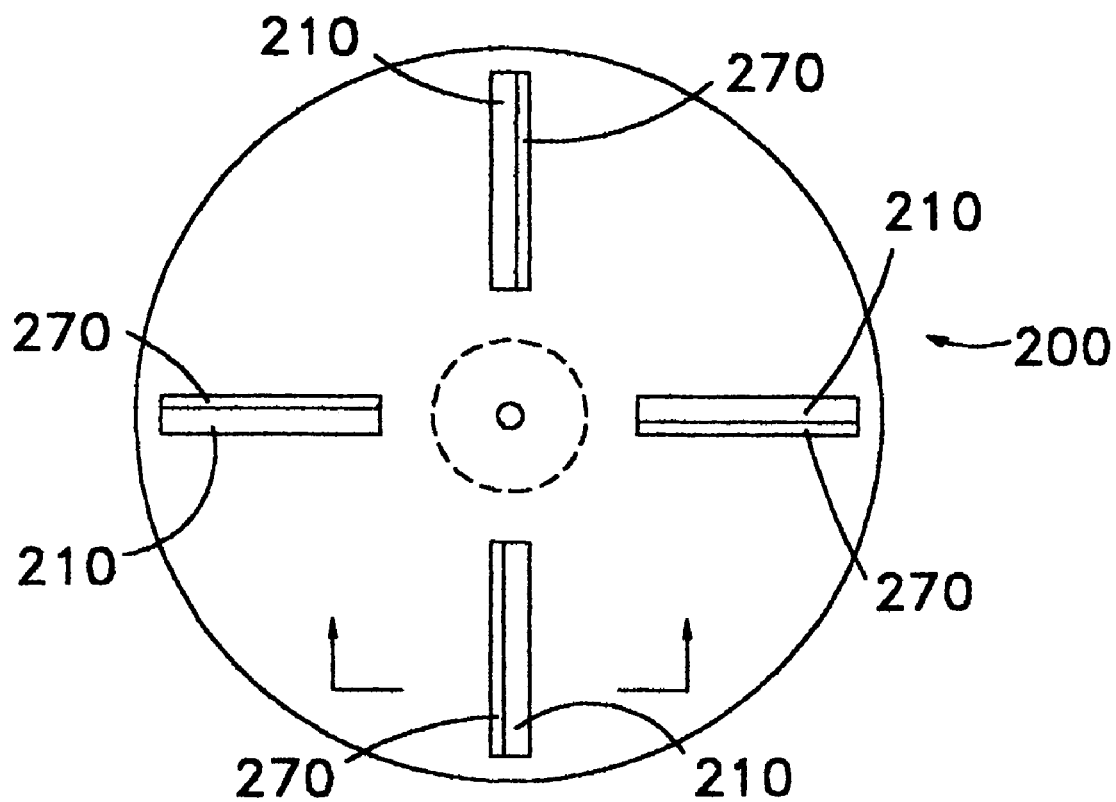
FIG. 5 is a view of a top surface of a blade for the medical waste disposal device.
Figure 6:
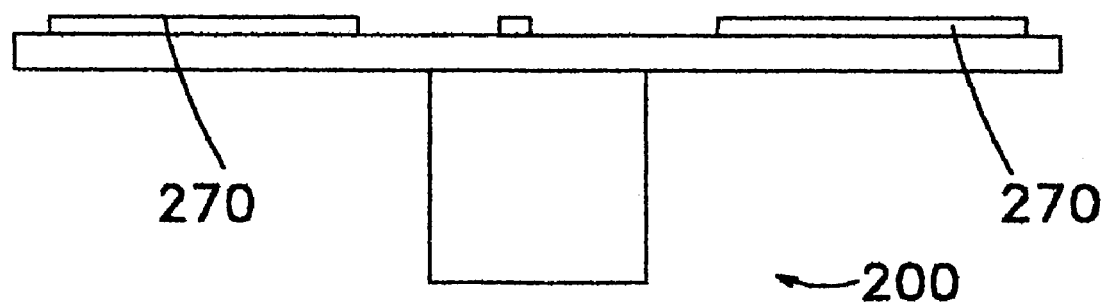
FIG. 6 is a side view of the blade.
Figure 7:
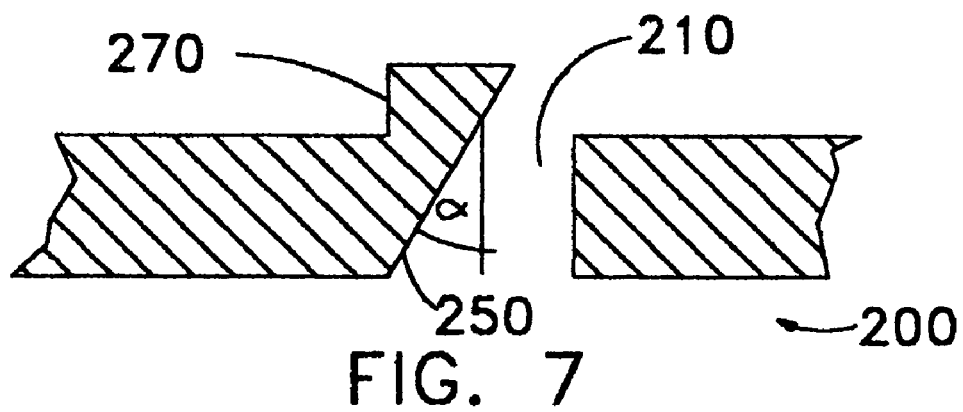
FIG. 7 is a cross-section view of the blade.

Turning now to FIGS. 5-7, a preferred embodiment for a blade 200 is shown. The blade 200 includes four openings 210. The openings 210 include a sharpened edge 250 and a raised portion 270.

Figure 8:
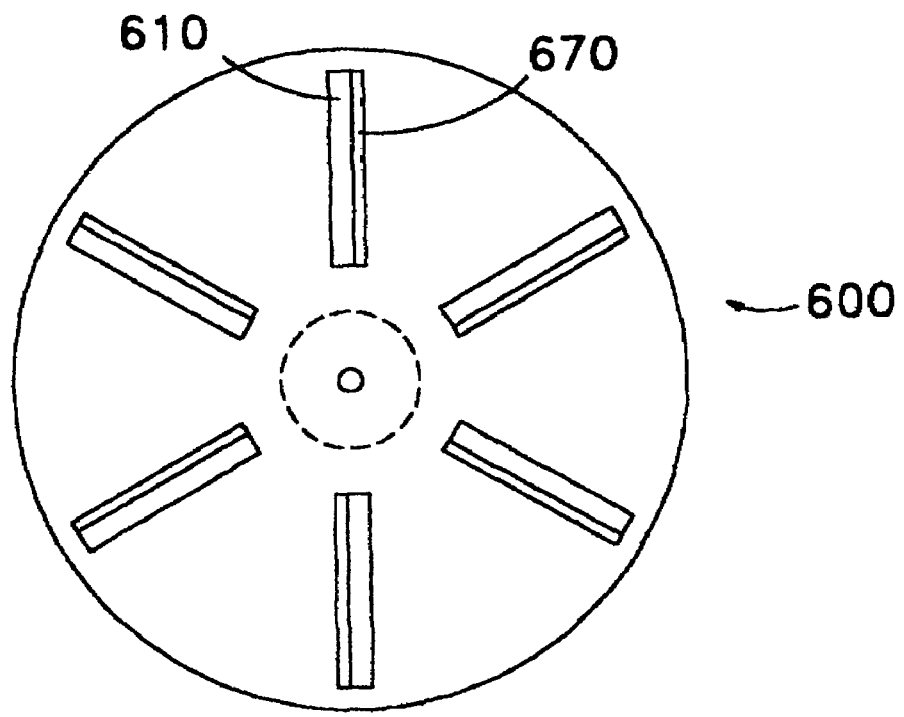
FIG. 8 is a view of a six-opening blade for the medical waste disposal device.

FIG. 8 shows a six opening blade 600 with openings 610 and raised portions 670.

Figure 9:
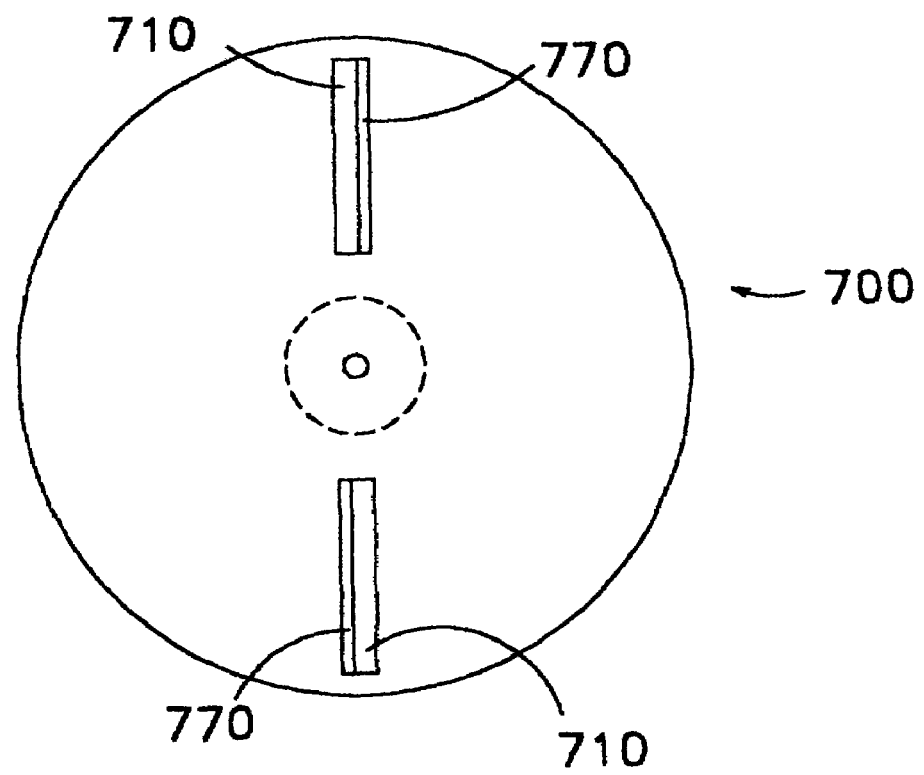
FIG. 9 is a view of a two-opening blade for the medical waste disposal device.
Figure 10:
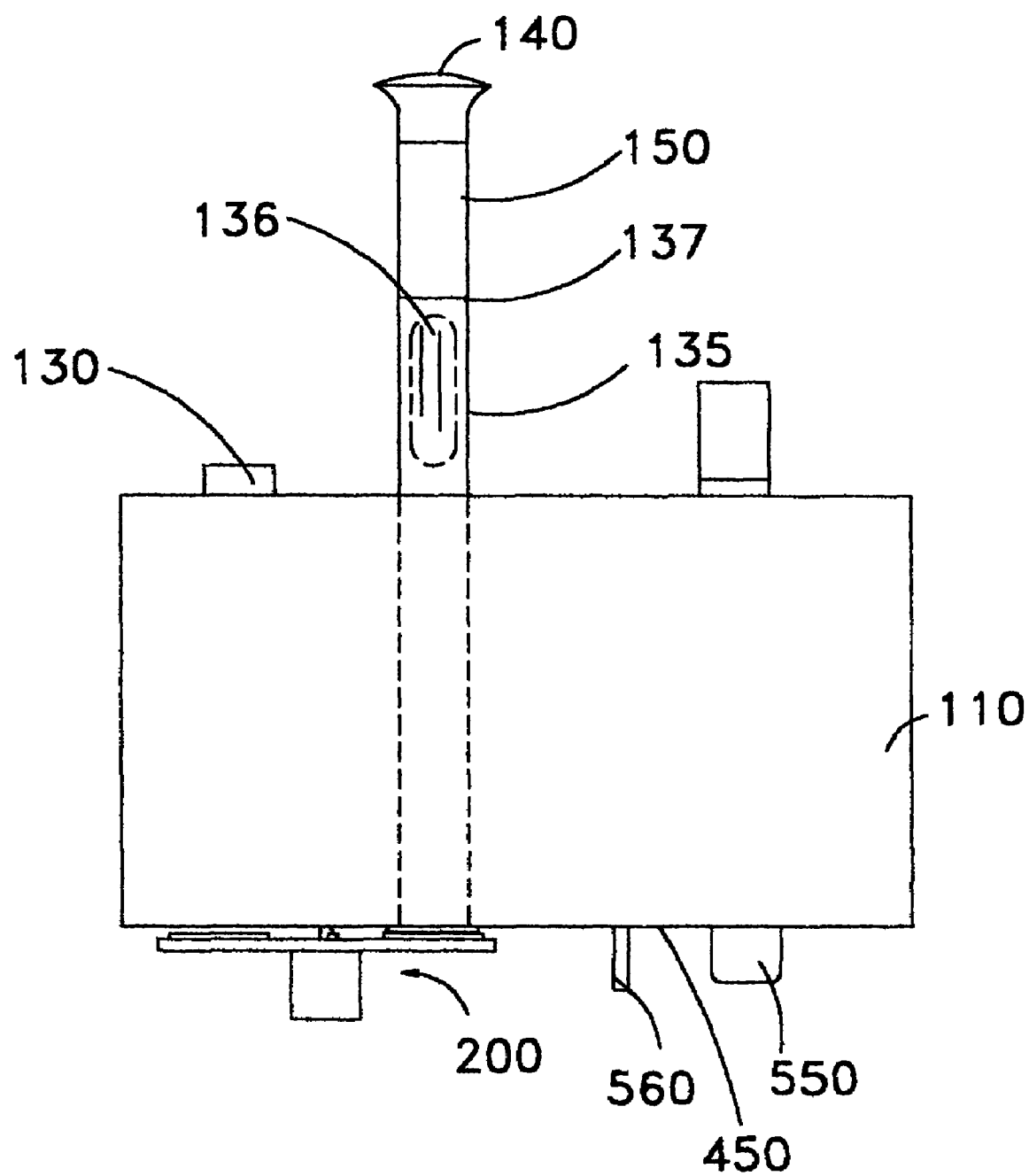
FIG. 10 is a side view of the upper housing with the blade attached.

FIG. 9 shows a two opening blade 700 with openings 710 and raised portions 770.

Figure 17:
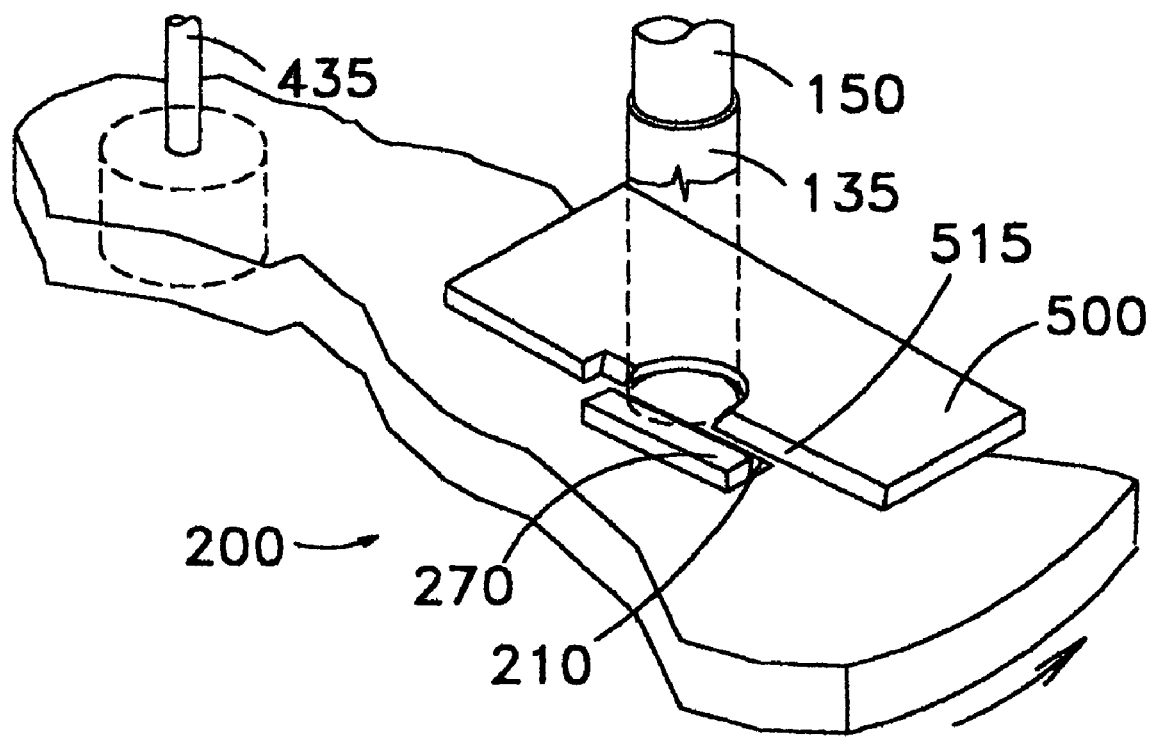
FIG. 17 shows the interaction of a cutting plate and the blade.
Figure 18:
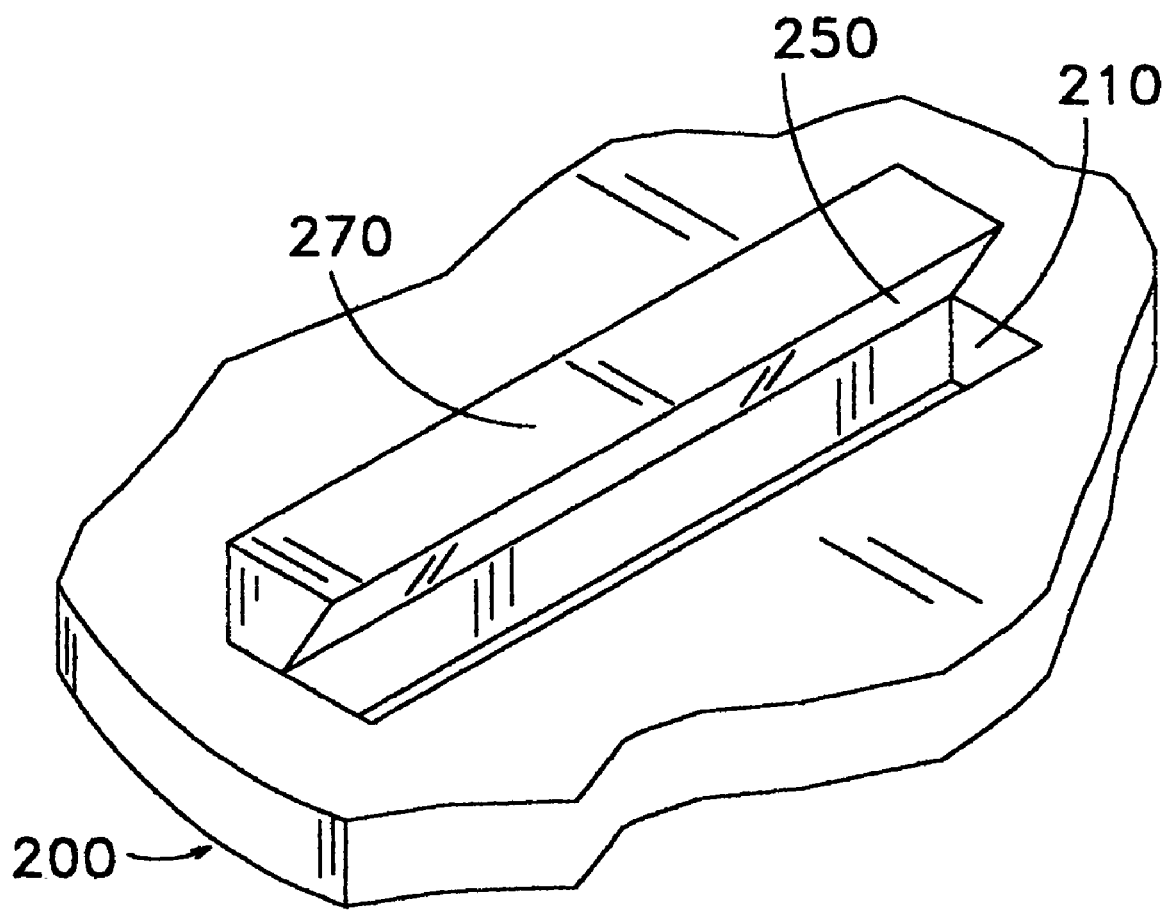
FIG. 18 is a detailed view of the opening and sharpened edge of the blade.
Figure 19:
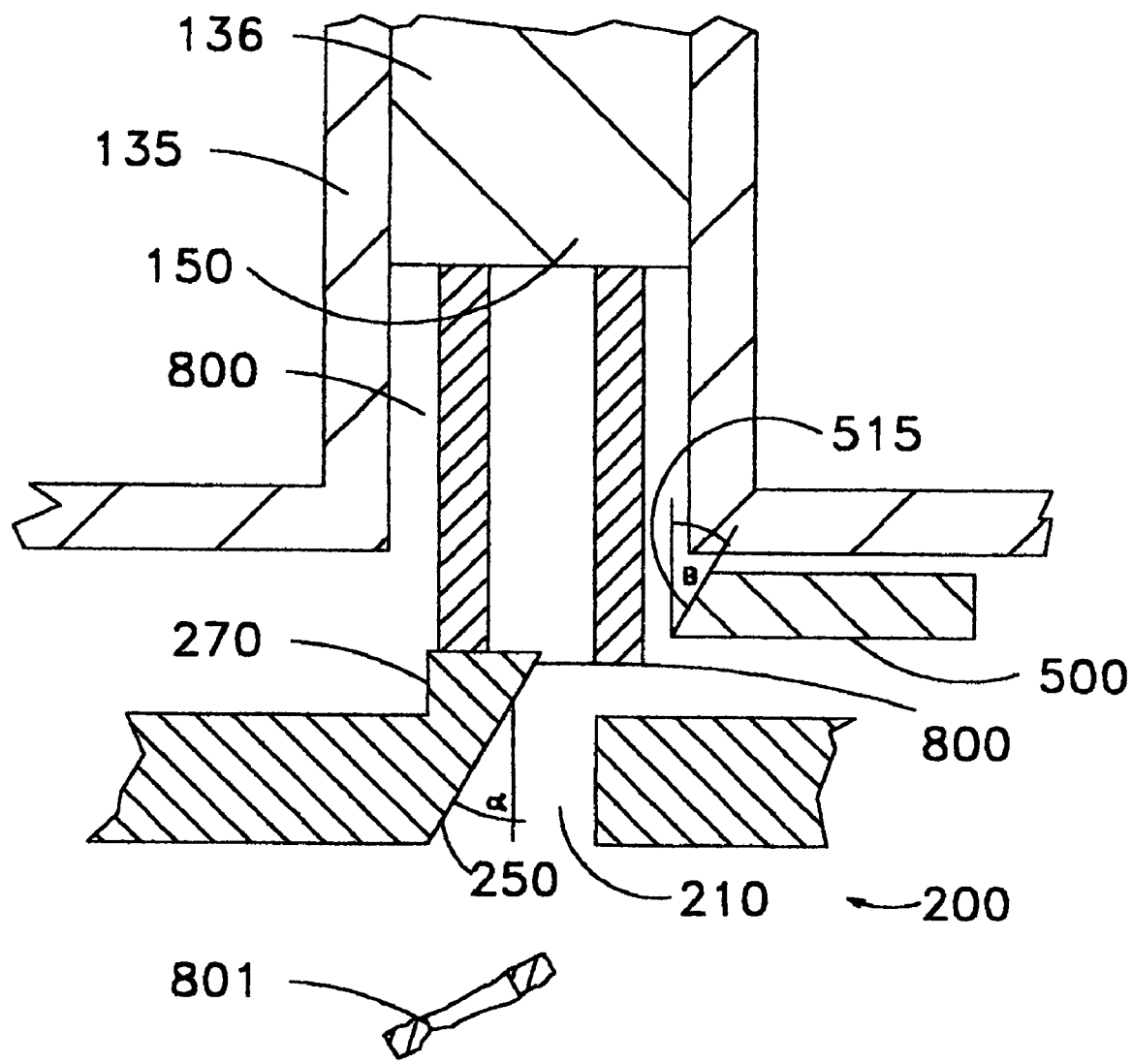
FIG. 19 is a sectional view showing the cutting mechanism of the present invention.

Turning now to FIGS. 10-20, the drop shaft 135 passes through the upper housing 110 until reaching a bottom surface 450 of the upper housing 110. There, an opening 460 in the bottom surface 450 provides passage for medical waste 800 to the blade 200, which is rotated by the drive shaft 435. The opening 460 is wholly defined by a cutting plate 500, i.e., the cutting plate fully circumscribes the opening 460. In other embodiments, the cutting plate 500 partially defines the opening 460, i.e. the cutting plate 500 only surrounds a portion of the opening 460. As shown in FIGS. 17-19, the cutting plate 500 includes a sharpened edge 515, which chops or scissors the medical waste in conjunction with the sharpened edge 250 of the blade. As shown in FIG. 17, the cutting plate 500 acts in conjunction and cooperation with the rotating blade 200 in chopping the medical waste 800, i.e., the sharpened edge 515 of the cutting plate 500 operates in conjunction and cooperation with the sharpened edge 250 of the blade 200 to chop or scissor the medical waste 800. As shown in FIG. 19, the raised portion 270 contacts the medical waste 800 being chopped by the blade 200 and the cutting plate 500 and pushes it away from the cutting plate 500 and through the opening 210 such that the chopping mechanism of the blade 200 and the cutting plate 500 do not jam with medical waste 800 and render the device inoperable. The action of the rotating blade 200 generally forces the chopped medical waste 801 through the opening 210 in the blade 200 into the lower housing 120. The action of the rotating blade 200 that generally forces the chopped medical waste through the opening 210 includes the force from the raised portion 270 striking the medical waste 800 with its sharpened edge 250 as well as the air current created by the rotation of the sharpened edge 250. Although the chopped medical waste 800 generally passes through the opening 210, it will be understood that small fragments or other minor amounts of debris from the medical waste may not immediately pass through the opening 210.

Figure 13:
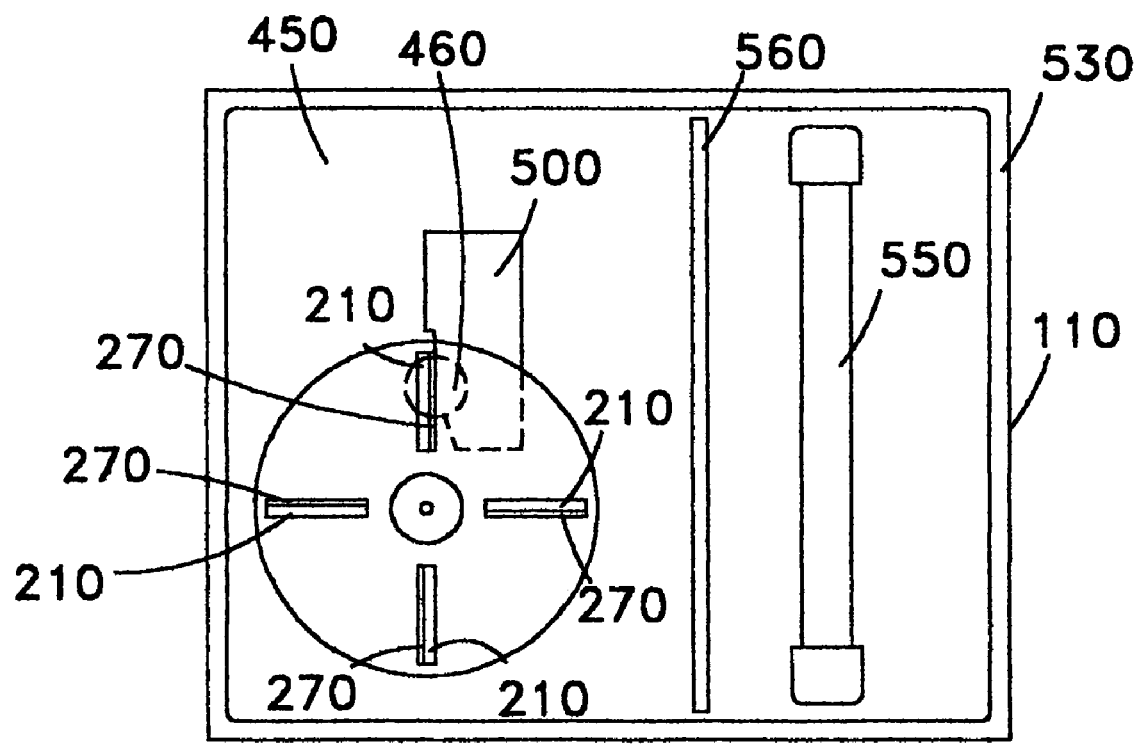
FIG. 13 is a bottom view of the upper housing.
Figure 14:
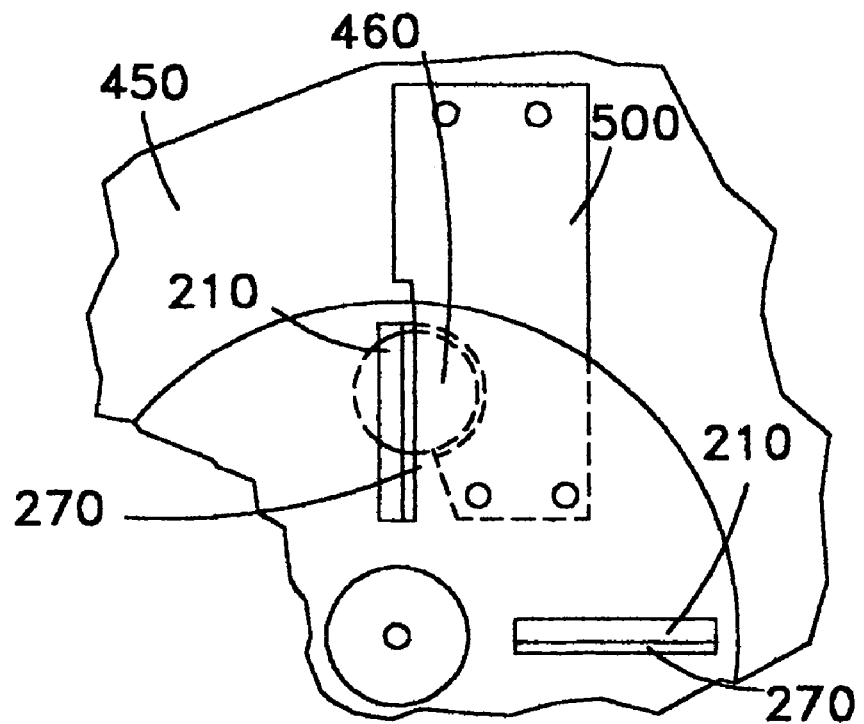
FIG. 14 is a close-up view of the bottom of the upper housing.
Figure 15:
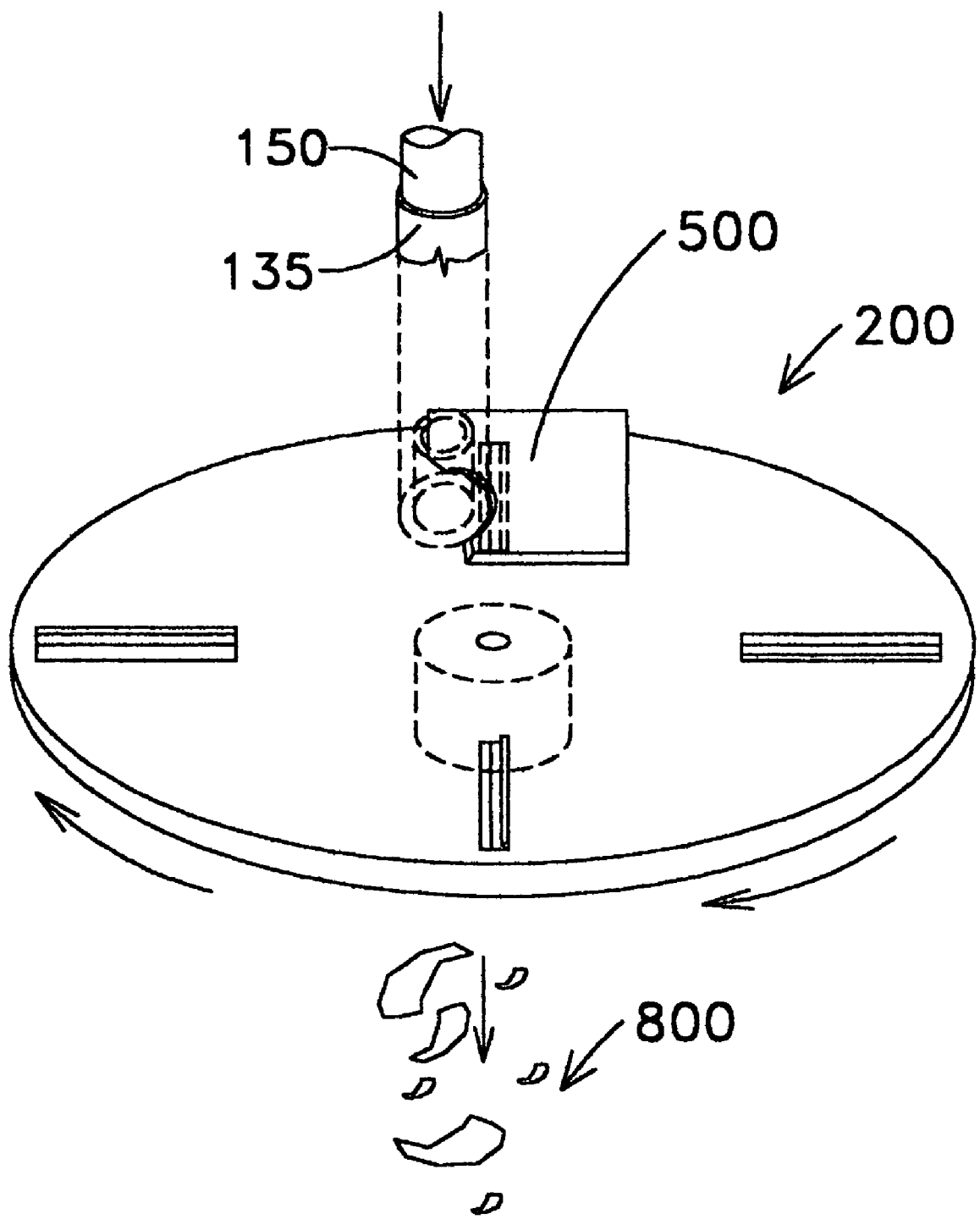
FIG. 15 is a view showing a cutting mechanism of the present invention.
Figure 16:
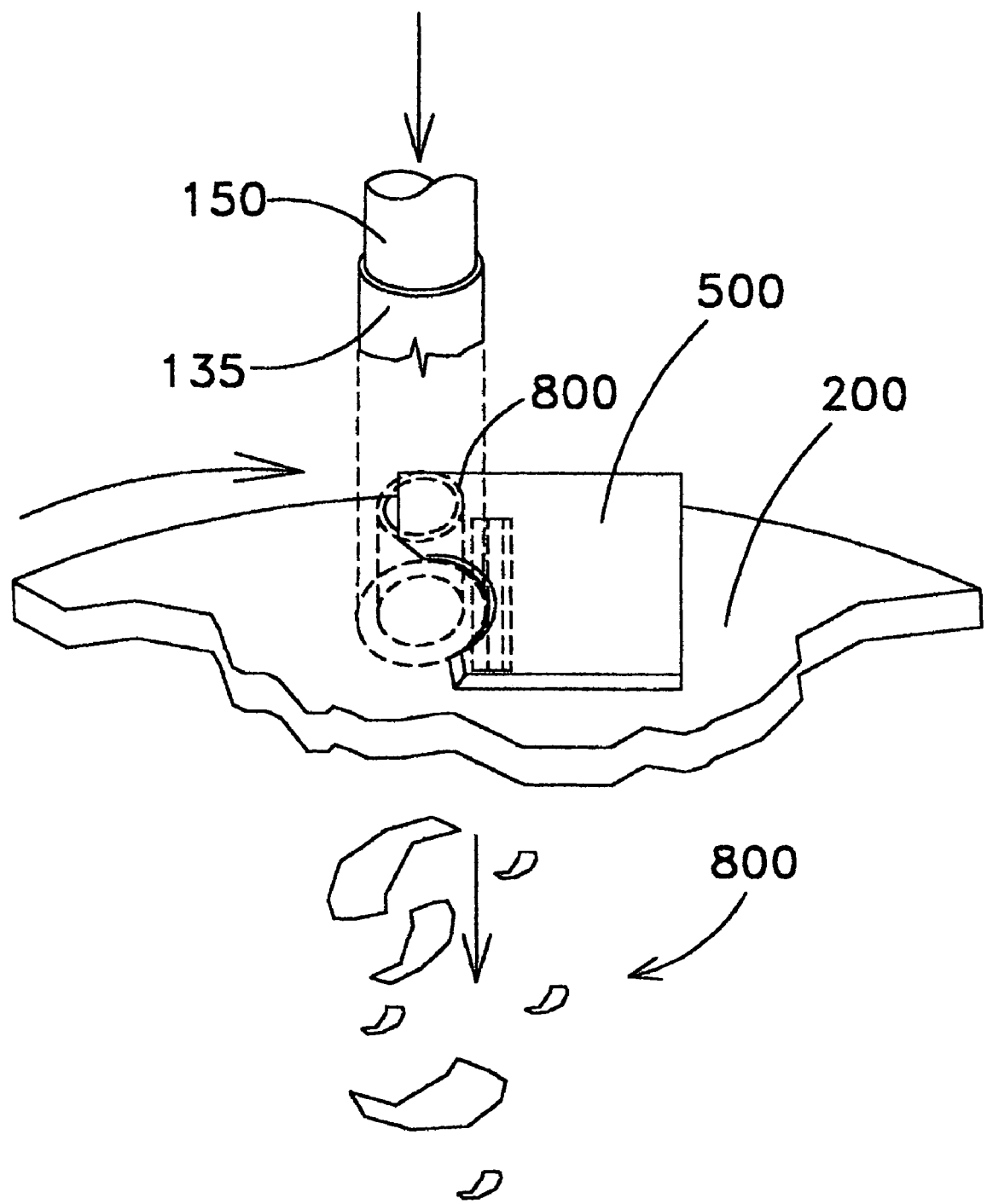
FIG. 16 is a close-up view of the cutting mechanism of the present invention.

A gasket 530 is shown in FIG. 13 which aids in sealing the junction of the upper housing 110 and the lower housing 120.

The bottom surface 450 also includes a UV light 550 and a plate 560 to prevent flying debris from the cutting process from striking and damaging the UV light 550.

A bottom 570 of the lower housing 120 collects the chopped medical waste. Preferably, the lower housing 120 is separable from the upper housing 110 by clips, latches, bolts and the like, such that the operator may remove and empty the reduced medical waste from the lower housing 120.

Figure 21:
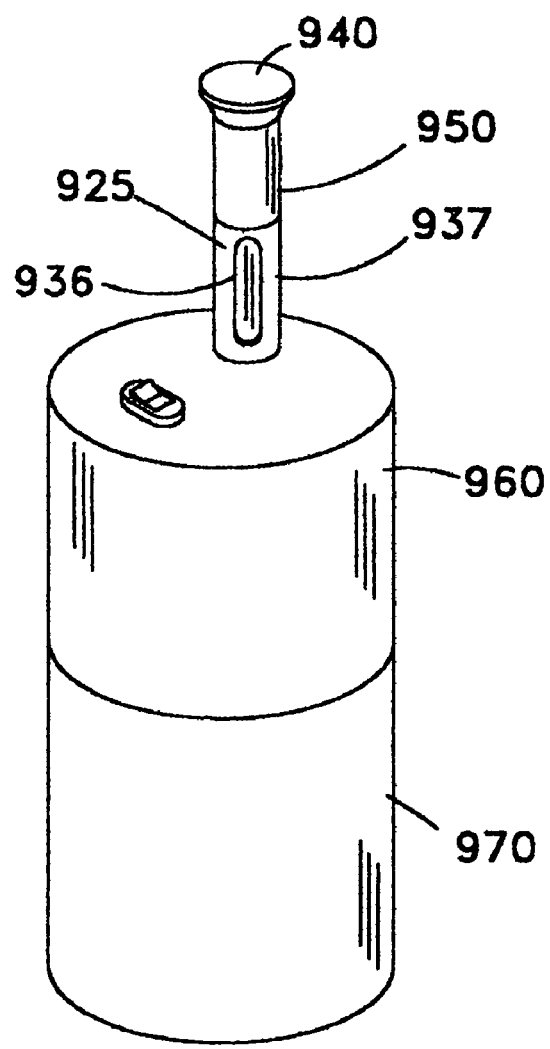
FIG. 21 is a view of a compact version of the present invention.
Figure 22:
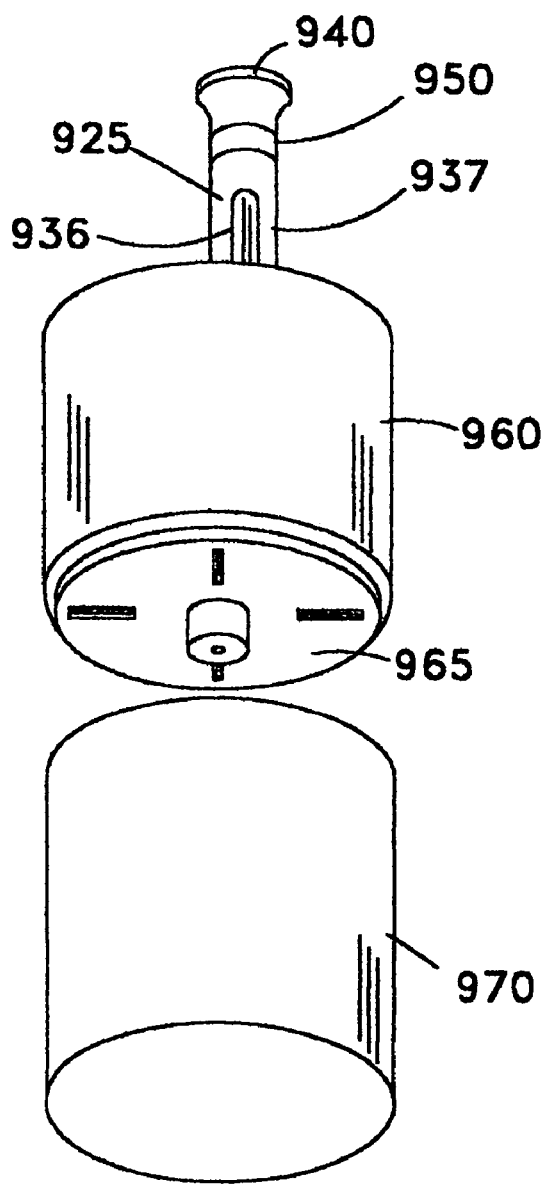
FIG. 22 is a view of the compact version with upper and lower housings separated.

FIGS. 21 and 22 describe a compact medical waste disposal device of the present invention. This particular embodiment of the device does not use a UV light. Otherwise, the compact medical waste disposal device is similar in operation and function to the other embodiments. This particular embodiment comprises an upper housing 960 and a lower housing 970. A blade 965 is shown to chop or scissor the medical waste. A drop shaft 925 is shown with an opening 936. The drop shaft 925 receives a plunger 950 with a handle 940. A drop shaft 925 receives the plunger 950 through a drop shaft collar 937.

Other embodiments of the present invention include a blade with multiple openings, with a portion of the openings not having a raised portion and/or a sharpened edge. These openings and/or the raised portion of the sharpened edge may be necessary for balancing the blade or for aerodynamic reasons.

The medical waste disposal device of the present invention is capable of chopping or scissoring all parts of a typical medical syringe, including the needle and the hub. Generally, no modifications are required to accommodate all types of medical waste. The medical waste disposal device of the present invention reduces syringes, catheters, lumens, tracheotomy tubes, blades, surgical needles, and associated plastic into a reduced volume that is capable of being recycled. The medical waste, after processing by the present invention, may be taken to a centrifugal separator for separating the metal from the plastic.

Prior art methods and devices of disposing medical waste include the bending of the syringe tip and the melting of the syringe tip. The present invention grinds the entire syringe including tip, hub, and reservoir. This provides an important advantage over the prior art as the operator is not required to physically touch the needle or bend the needle or remove the needle from the remainder of the syringe, thus reducing the likelihood of an unintentional needle prick that could contaminate the user with germs and/or bacteria.

Other prior art devices are prone to jamming for a variety of reasons, such as poor design of its grinding mechanisms. Other prior art devices are simply too large and require too much electrical current to be feasible for hospital room use.

As evident from the foregoing description, certain aspects of the present invention are not limited by the particular details of the examples illustrated herein, and it is therefore contemplated that other modifications and applications, or equivalents thereof, will occur to those skilled in the art. It is accordingly intended that all claims shall cover all such modifications and applications that do not depart from the spirit and the scope of the present invention.

What is claimed:

1. A medical waste disposal device, comprising: a rotating blade comprising: one or more openings, wherein one of the or more openings has a first sharpened edge and at least one raised portion that is adjacent to the one opening; a motor for rotating the blade; a drop shaft leading to an opening in a surface of the device; and the surface comprising a cutting plate with a second sharpened edge, wherein the opening in the surface is wholly or partially defined by the cutting plate.

2. The medical waste disposal device according to claim 1, wherein medical waste is chopped or scissored between the first sharpened edge and the second sharpened edge while the raised portion pushes the chopped medical waste away from the first and the second sharpened edges in the chopping or scissoring of the medical waste.

3. The medical waste disposal device according to claim 1, wherein the blade comprises two to eight openings.

4. The medical waste disposal device according to claim 1, wherein a housing comprises an upper housing and a lower housing, wherein a bottom surface of the upper housing comprises the cutting plate.

5. The medical waste disposal device according to claim 1, wherein the medical waste disposal device reduces syringes, catheters, lumens, tracheotomy tubes, blades or surgical needles.

6. The medical waste disposal device according to claim 1, wherein the medical waste disposal device operates on direct current.

7. The medical waste disposal device according to claim 1, wherein the medical waste disposal device reduces the volume of medical waste in a ratio of about 500-to-1.

8. The medical waste disposal device according to claim 1, wherein the medical waste disposal device rotates the blade at approximately 1,000 rpm to approximately 10,000 rpm.

9. The medical waste disposal device according to claim 1, further comprising a housing, wherein the medical waste disposal device creates a cyclonic action that creates a down draft to push the chopped particles to the bottom of the housing, and the down draft and the cyclonic action create an up draft on peripheral edges of the housing and up over the blade and back again to the bottom of the housing.

10. The medical waste disposal device according to claim 9, wherein the cyclonic action cleans the blade and reduces the occurrence of medical waste jamming in the blade.

11. The medical waste disposal device according to claim 1, wherein the drop shaft directs medical waste in a vertical manner to the blade.

12. The medical waste disposal device according to claim 1, wherein the medical waste disposal device operates on 12-volt direct current.

13. The medical waste disposal device according to claim 12, wherein the medical waste device is portable.

14. The medical waste disposal device according to claim 1, wherein the first sharpened edge of the blade is sharpened at an angle of approximately 10° to approximately 90°.

15. The medical waste disposal device according to claim 1, wherein the raised portion contacts the medical waste being chopped by the blade and pushes it away from the cutting plate such that the chopping mechanism of the blade and the cutting plate do not jam with medical waste.

16. The medical waste disposal device according to claim 1, wherein the one or more openings are generally rectangular or ovular in shape.

17. The medical waste disposal device according to claim 1, wherein the medical waste is chopped or scissored between the first and second sharpened edges while the raised portion pushes the medical waste away from the sharpened edges and through the at least one opening in the blade.

18. The medical waste disposal device according to claim 1, wherein the blade comprise two or more openings having the raised potion and the first sharpened edge.

19. The medical waste disposal device according to claim 1, wherein the blade comprises one opening having the raised portion and the first sharpened edge and another opening without the raised portion or the first sharpened edge.

20. A medical waste disposal device, comprising: a rotating blade comprising: one or more openings, wherein one of the one or more openings has a first sharpened edge and at least one raised portion that is adjacent to the one opening; a motor for rotating the blade; a housing that comprises the motor and the blade; a drop shaft that passes through the housing until reaching a bottom surface of the housing; and an opening in the bottom surface provides passage for medical waste to the blade, wherein the bottom surface comprises a cutting plate with a second sharpened edge, wherein the opening in the bottom surface is wholly or partially defined by the cutting plate.

21. A medical waste disposal device, comprising: a rotating blade comprising: one or more openings, wherein one opening of the one or more openings has a first sharpened edge and at least one raised portion that is adjacent to the one opening; a motor for rotating the blade; a housing that comprises a lower housing and an upper housing, wherein the upper housing comprises the motor and the lower housing comprises the blade and contains the chopped or scissored medical waste; and a drop shaft passes through the upper housing until reaching a bottom surface of the upper housing, the bottom surface comprising a cuffing plate with a second sharpened edge and an opening is in the bottom surface and provides passage for the medical waste to the blade, wherein the opening is wholly or partially defined by the cutting plate.

22. The medical waste disposal device according to claim 21, wherein a drive shaft from the motor protrudes into the lower housing and the blade is connected or attached to the drive shaft.

23. A medical waste disposal device, comprising: a rotating blade comprising: one or more openings, wherein one of the one or more openings has a first sharpened edge and at least one raised portion that is adjacent to the one opening; an upper housing comprising a motor for rotating the blade; the upper housing comprising a drop shaft leading to an opening in a surface of the device; and the surface comprising a cutting plate with a second sharpened edge, wherein the cutting plate wholly or partially defines the opening in the surface, wherein the medical waste disposal device comprises a UV light in a lower housing.

24. A medical waste disposal device, comprising: a drop shaft leading to a rotating blade comprising: one or more openings, wherein one of the one or more openings has a first sharpened edge and at least one raised portion that is adjacent to the one opening; a motor for rotating the blade; and a cutting plate with a second sharpened edge, wherein the medical waste disposal device comprises a UV light on a lower portion of an upper housing to disinfect or sterilize chopped or scissored medical waste.

25. A medical waste disposal device, comprising:
a housing,
a motor in a rotational engagement with a blade, the blade comprising a raised portion and an opening with a first sharpened edge,
a drop shaft directing medical waste to an opening in a surface with the housing,
a cutting plate with a second sharpened edge integral to or attached to the housing, wherein the cutting plate wholly or partially defines the opening in the surface of the housing, and
wherein the drop shaft has a vertical orientation and an axis of rotation of the blade is perpendicular to the drop shaft.

26. A medical waste disposal device, comprising:

an upper housing and a lower housing;

a drop shaft passing through the upper housing and in open communication with an opening in a bottom surface of the upper housing, wherein the bottom surface comprises a cutting plate that wholly or partially defines the opening in the bottom surface of the upper housing;

the upper housing comprising a motor in rotational engagement with a blade beneath the bottom surface of the upper housing;

the blade comprising a raised portion and a blade opening with a first sharpened edge; and the cutting plate comprising a second sharpened edge.

* * * * *

UNITED STATES PATENT AND TRADEMARK OFFICE
CERTIFICATE OF CORRECTION

| | | |
|---|---|---|
| PATENT NO. | : 7,360,730 B2 | |
| APPLICATION NO. | : 10/891396 | |
| DATED | : April 22, 2008 | |
| INVENTOR(S) | : James S. Brown | |

It is certified that error appears in the above-identified patent and that said Letters Patent is hereby corrected as shown below:

In the Claims

Column 7, lines 19-20, Claim 1, after "wherein one of the" and before "or more openings" insert -- one --

Column 8, lines 21-22, Claim 18, delete "comprise" and insert -- comprises --; delete "potion" and insert -- portion --

Signed and Sealed this
Seventh Day of May, 2013

Teresa Stanek Rea
*Acting Director of the United States Patent and Trademark Office*